United States Patent [19]

Yamazaki et al.

[11] Patent Number: 5,023,550
[45] Date of Patent: Jun. 11, 1991

[54] ROTATING HEAD MECHANISM OF ROTARY TYPE AC MAGNETIC FLUX LEAKAGE FLAW DETECTOR

[75] Inventors: Makoto Yamazaki; Kazumi Ueda; Shinichi Isobe; Katsunari Sato, all of Tokyo, Japan

[73] Assignee: Eddio Corporation, Tokyo, Japan

[21] Appl. No.: 473,606

[22] Filed: Feb. 1, 1990

[30] Foreign Application Priority Data

Feb. 22, 1989 [JP] Japan .................................. 1-42465

[51] Int. Cl.⁵ ...................... G01N 27/87; G01R 33/12
[52] U.S. Cl. ..................... 324/262; 324/232; 324/242
[58] Field of Search ............... 324/232, 242, 243, 260, 324/262

[56] References Cited

U.S. PATENT DOCUMENTS

| | | |
|---|---|---|
| 2,998,566 | 8/1961 | Cochran . |
| 3,025,460 | 3/1962 | Callan et al. ........................ 324/260 |
| 3,202,914 | 8/1965 | Deem et al. . |
| 3,299,349 | 1/1967 | Tompkins et al. . |
| 3,612,987 | 10/1971 | Placke et al. ........................ 324/242 |
| 3,736,501 | 5/1973 | Donkin .............................. 324/242 |
| 4,218,651 | 8/1980 | Ivy . |

FOREIGN PATENT DOCUMENTS

| | | | |
|---|---|---|---|
| 0785723 | 12/1980 | U.S.S.R. ............... | 324/262 |
| 2034049 | 5/1980 | United Kingdom ............... | 324/262 |

Primary Examiner—Gerard R. Strecker
Attorney, Agent, or Firm—Fleit, Jacobson, Cohn, Price, Holman & Stern

[57] ABSTRACT

A rotating head mechanism of a rotary type AC magnetic flux leakage flaw detector comprises a rotating disc which has an opening for passing a test piece for flaw detection, mounting frames which are disposed in the rotating disc so as to oppose to each other with the opening located therebetween, shafts which are rotatably disposed across the mounting frames and each of which has external threads of senses opposite to each other at a position on one side of the opening and a position on the other side thereof, a first nut which engages the external thread of one sense in the external threads of each shaft, a second nut which engages the external thread of the other sense in the external threads of each shaft, a first cradle which is coupled to the first nuts, a second cradle which is coupled to the second nuts, a first exciting magnetic poles/detecting probes-assembly which is mounted on the first cradle, a second exciting magnetic poles/detecting probes-assembly which is mounted on the second cradle, and rotation drive means for rotating the shafts. When the shafts are rotated by the rotation drive means, the first and second nuts are moved in a direction in which they come near to each other or away from each other along the shafts, thereby making it possible to change an opposing spacing in a diametrical direction of the opening, between the first and second exciting magnetic poles/detecting probes-assemblies respectively mounted on the first and second cradles.

4 Claims, 4 Drawing Sheets

ROTATING HEAD MECHANISM OF ROTARY TYPE AC MAGNETIC FLUX LEAKAGE FLAW DETECTOR

BACKGROUND OF THE INVENTION

1. Field of the Invention

The present invention relates to the rotating head mechanism of a rotary type AC magnetic flux leakage flaw detector.

2. Description of the Prior Art

Regarding wire rods, steel bars, etc. which include a material of comparatively small diameter having the maximum diameter of 30 mm or 40 mm by way of example, a material stretched with a die by the use of a wire stretcher, a material drawn with a die as in the wire stretcher by a combined machine, and so on; the grain of the outer surface of the material is good so as to exhibit a surface roughness of 5–10 S (a ruggedness of 5–10 μm), the piece of the material to-be-tested has a favorable circularity and has a small diametrical deviation, and the dimensional accuracy of the material is high in such a manner that the magnitude of a bend in the lengthwise direction of the material is 1–2 mm/m. As to such a piece to-be-tested, accordingly, the centering between a rotating probe and the test piece is easy, and the distance between the rotating probe and the outer surface of the test piece is easily maintained within a predetermined allowable range. Therefore, a satisfactory flaw detection accuracy can be guaranteed even with the automatic eddy-current flaw detection which employs the rotating probe. It is known, however, that, in general, all the factors of the surface grain behavior, the circularity and the bend of the test piece worsen more as the outer diameter of the test piece becomes larger. By way of example, a steel bar whose outer diameter is about 50–60 mm is manufactured in such a way that hot-rolled steel left intact is cooled and that the bend is merely corrected by a straightening machine. The roughnesses of the outer surfaces of some of such steel bars reach 15 S–300 S or 500 S (15 μm–300 μm or 500 μm). Besides, the bent magnitude per unit length is large and sometimes reaches 2–3 mm/m or 3–4 mm/m. In order to automatically detect dotty flaws in the surface of such a test piece, a linear flaw extending in the rolled direction thereof, etc., a rotary flaw detector which rotates a plurality of probes and which can advance the test piece straightforward to obtain helical flaw detection traces can be used as in the foregoing case. Since, however, the dimensional accuracy of the test piece is not favorable in contrast to the foregoing case, there is the problem that a mechanism for the centering between the test piece and the rotating probes needs to be contrived. Also, there is the problem that the grain property of the surface of the test piece is not applicable to the eddy-current flaw detection of the prior art based on the rotating probes. More specifically, the mechanical dimensional accuracy is inferior for such a reason that the hot-rolled surface left intact is uneven and has iron oxide chips (scales) adhering thereto. Besides, the inhomogeneous state of the electromagnetic surface behavior renders it difficult to detect linear flaws (seams, hair cracks and longitudinal cracks) in mass formation which flaws have an opening of a small width by the prior-art eddy-current flaw detection means.

Therefore, various technical improvements have heretofore been made for the detections of the surface flaws of the hot-rolled steel materials of inferior surface grain behaviors. Among them, a magnetic flux leakage flaw detection method is known as replacing fluorescent magnetic powder flaw detection based on visual inspection. As means for magnetizing the steel piece in the flux leakage flaw detection, there are known a D.C. flux leakage, an A.C. magnetic flux leakage, and the combination of them. Here, the D.C. flux leakage method has the merit that both the flaws of the inner surface and outer surface of a steel tube or the like can be detected, but it is problematic in the following points:

(1) During a flaw detection operation, the attractive force of a D.C. electromagnet exerts an evil effect to spoil the mechanical centering between the tube being inspected and exciting magnetic poles.

(2) As a higher flaw detection accuracy is intended, the value of ampere-turns to be applied to the D.C. electromagnet must be increased more, with the result that the exciting magnetic poles and the electromagnet overheat due to Joule heat.

(3) The flaw detection accuracy is limited to a flaw depth of about 0.3 mm–0.2 mm as the lower limit value, and it has been empirically known that the method cannot meet the demands of industrial circles of which the detection of still shallower flaws is required.

On the other hand, the conventional A.C. magnetic flux leakage method usually employs a magnetosensitive device, for example, a Sony magnetodiode or a Hall effect device. Such a device is subject to a restricted frequency response characteristic inherent in a semiconductor, the upper limit of an exciting frequency to be applied to the device is 2 kHz or 3 kHz, and the flaw detection accuracy of the device in terms of the detection capability thereof is limited to a flaw depth of about 0.3 mm–0.2 mm. As an expedient for overcoming this limit of the detection capability, it has heretofore been proposed that a search coil (sensor probe) of small diameter is employed as a detecting device corresponding to frequencies for wide applications, whereupon the exciting frequency to be applied is set as high as 4–16 kHz. Thus, the depth of magnetization directly under the surface of a test piece is reduced by the skin effect, whereby excitation energy is focused into the bounds of a depth required for flaw detection, and a high flux density is established by the focusing. As a result, an AC magnetic flux leakage from a minute flaw part is increased to enhance the detection capability.

Although the magnetic flux leakage flaw detection method is more suited to the flaw detection of the hot-rolled steel material or the like of inferior surface grain behavior than the eddy-current flaw detection method, it has the large number of problems to-be-solved as stated before. Particularly in a rotary type flux leakage flaw detector, exciting magnetic pole portions and a group of detecting probes need to be held in a predetermined mechanical positional relationship. Moreover, unless the group of detecting probes and the exciting magnetic pole portions are kept withdrawn during rotation till the arrival of the fore end of the steel material being the test piece, they might be damaged by the fore end of the steel material. Accordingly, the rotary type flux leakage flaw detector necessitates a mechanical coupling/interlocking setup which can hold the exciting magnetic pole portions and the group of detecting probes in the predetermined mechanical positional relationship and can withdraw them from the test piece on the necessary occasion.

As such mechanical coupling/interlocking setups, there have hitherto been proposed ones wherein, using an electromagnet or a rotary solenoid, the detecting probes are made free to retract and are thus prevented from damaging, as disclosed in the specification of U.S. Pat. No. 3,299,350, the specification of U.S. Pat. No. 3,612,987, and the official gazette of Japanese Patent Application Publication No. 48-36916. In addition, the official gazette of Japanese Patent Application Publication No. 51-44675 discloses a setup wherein exciting coils and detecting devices are mounted on a rotating disc and wherein pinch rollers adapted to be pneumatically operated are arranged before and behind the disc in the passing direction of a test piece so as to restrain the test piece, thereby intending to detect a flaw stably. Further, the specification of U.S. Pat. No. 4,297,636 discloses a setup wherein a yoke lever and a probe lever are disposed indendently of a magnet yoke and a probe support and wherein the yoke lever is set to a closed position by a fore-end bent portion provided in a stopper plate, thereby making it possible to protect the magnet yoke from any hindrance in the movement of the yoke lever in the opening direction thereof. With this setup, the probe lever is installed by the turning pin of a pin holding plate which is fixed to a part of the yoke lever, and a counterweight is mounted on the opposite side to probes with respect to the fulcrum.

Any of the rotating head mechanisms of the rotary type flux leakage flaw detectors hitherto proposed as mentioned above is such that exciting magnetic pole portions and a group of detecting probes are fixedly mounted on a rotating disc. Therefore, in case of detecting the flaw of a test piece of different outer diameter, such a troublesome operation has been involved that the exciting magnetic pole portions and the group of detecting probes are adjusted so as to be appropriate for the outer diameter or that they are replaced with others appropriate for the outer diameter.

An object of the present invention is to provide the rotating head mechanism of a rotary type leakge-flux flaw detector which can eliminate the problems of the prior-art techniques as stated before.

SUMMARY OF THE INVENTION

According to this invention, there is provided a rotating head mechanism of a rotary type AC magnetic flux leakage flaw detector, comprising a rotating disc which has an opening for passing a test piece for flaw detection, mounting frames which are disposed in the rotating disc so as to oppose to each other with the opening located therebetween, shafts which are rotatably disposed across the mounting frames and each of which has external threads of senses opposite to each other at a position on one side of the opening and a position on the other side thereof, a first nut which engages the external thread of one sense in the external threads of each shaft, a second nut which engages the external thread of the other sense in said external threads of each shaft, a first cradle which is coupled to the first nuts, a second cradle which is coupled to the second nuts, a first exciting magnetic poles/detecting probes-assembly which is mounted on the first cradle, a second exciting magnetic poles/detecting probes-assembly which is mounted on the second cradle, and rotation drive means for rotating the shafts, wherein when the shafts are rotated by the rotation drive means, the first and second nuts are moved in a direction in which they come near to each other or away from each other along the shafts, thereby making it possible to change an opposing spacing in a diametrical direction of the opening, between the first and second exciting magnetic poles/detecting probes-assemblies respectively mounted on the first and second cradles.

This invention will now be described in further detail with regard to preferred embodiments as illustrated in the accompanying drawings.

BREIF DESCRIPTION OF THE DRAWINGS

DESCRIPTION OF THE PREFERRED EMBODIMENTS

Figure 1:
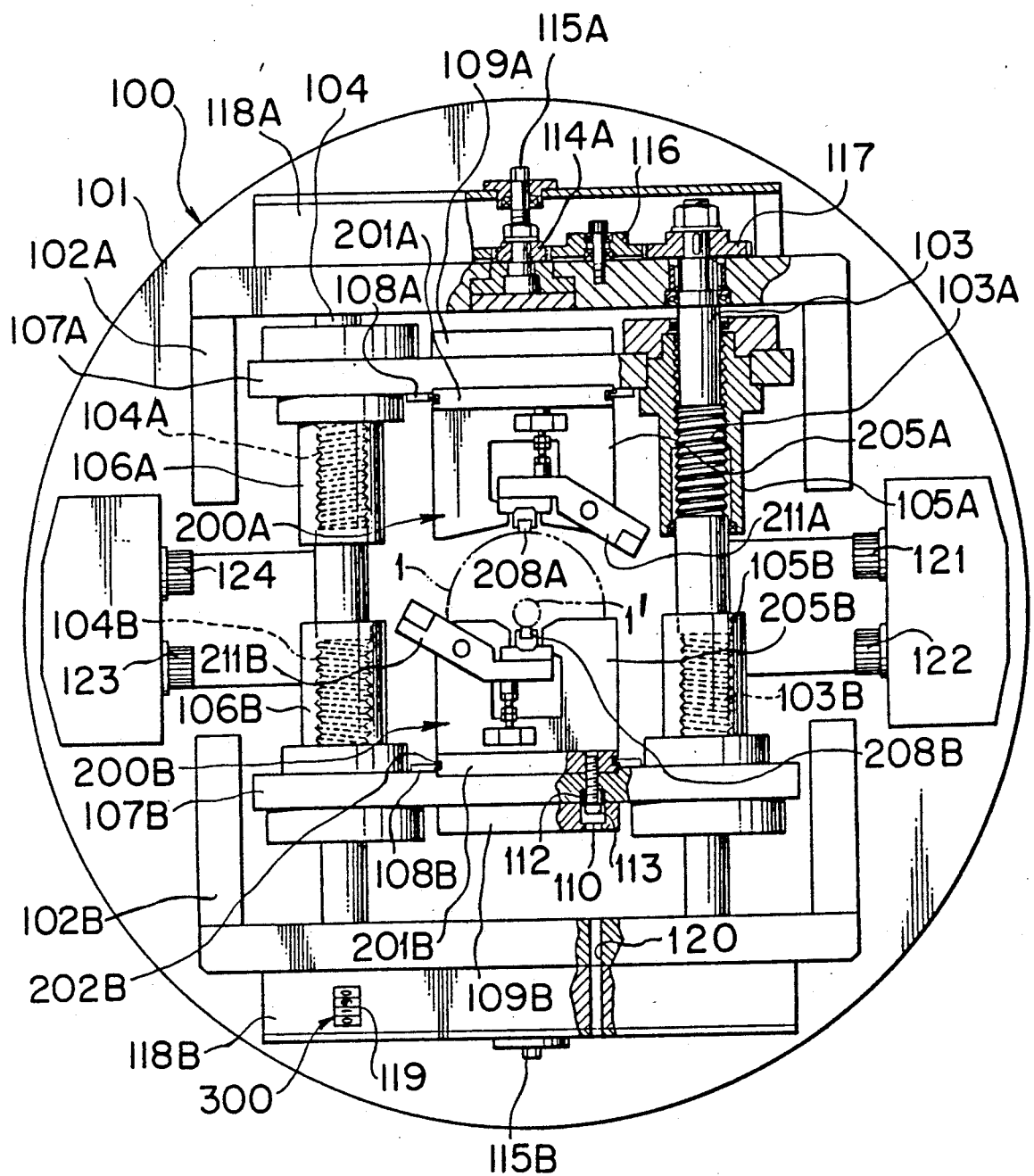
FIG. 1 is a schematic front view of the rotating head mechanism of a rotary type AC magnetic flux leakage flaw detector which is an embodiment of the present invention.

As shown in FIG. 1, the rotating head mechanism of this embodiment comprises a rotating disc 101 which is driven and rotated by the rotation driver of the rotary type AC magnetic flux leakage flaw detector (hereinafter referred to as MFL flaw detector). The rotating disc 101 is centrally formed with a central opening, not shown, for passing therethrough a test piece to have its flaw detected. In addition, a pair of upper and lower mounting frames 102A and 102B are fixedly provided on the front surface of the rotating disc 101 in a manner to oppose to each other with the central opening located therebetween. A pair of right and left shafts 103 and 104 which extend in parallel with each other on both the sides of the central opening of the rotary disc 101 are rotatably mounted across the mounting frames 102A and 102B. Here, the shaft 103 is formed with a right-handed external thread 103A at a position above the central opening and a left-handed external thread 103B at a position below the central opening. Likewise, the shaft 104 is formed with a right-handed external thread 104A at a position above the central opening and a left-handed external thread 104B at a position below the central opening. A right-handed nut 105A is held in engagement with the right-handed external thread 103A of the shaft 103, while a left-handed nut 105B is held in engagement with the left-handed external thread 103B, and a right-handed nut 106A is held in engagement with the right-handed external thread 104A of the shaft 104, while a left-handed nut 106B is held in engagement with the left-handed external thread 104B. A magnet yoke cradle 107A is extended across the upper right nut 105A and the upper left nut 106A. Also, a magnet yoke cradle 107B is extended across the lower right nut 105B and the lower left nut 106B. A pair of right and left guides 108A are provided on the lower surface of the magnet yoke cradle 107A, while a pair of right and left guides 108B are similarly provided on the upper surface of the magnet yoke cradle 107B. An exciting magnetic poles/detecting probes-assembly 200A to be described later is detachably mounted on the yoke cradle 107A so as to engage the guides 108A, while an exciting magnetic poles/detecting probes-assembly 200B to be described later is detachably mounted on the yoke cradle 107B so as to engage the guides 108B.

The upper mounting frame 102A is furnished with a gear cover 118A. Disposed centrally of the upper mounting frame 102A is a gear 114A which is rotated by a drive shaft 115A adapted to be rotated externally of the gear cover 118A. Intermediate gears 116 each of which meshes with the gear 114A, are disposed at the right and left of this gear 114A. Gears 117 are mounted on the upper ends of the shafts 103 and 104, and they are held in mesh with the respectively corresponding intermediate gears 116. Likewise, the lower mounting frame 102B is furnished with a gear cover 118B, and a gear similar to the gear 114A, which is rotated by a drive shaft 115B adapted to be rotated externally of the gear cover 118B, is disposed centrally of the lower mounting frame 102B. Gears similar to the intermediate gears 116, each of which meshes with this gear similar to the gear 114A, are disposed at the right and left of this gear. Gears similar to the gears 117 are also mounted on the lower ends of the shafts 103 and 104, and these gears 117 are held in mesh with the respectively corresponding intermediate gears 116.

Figure 2:
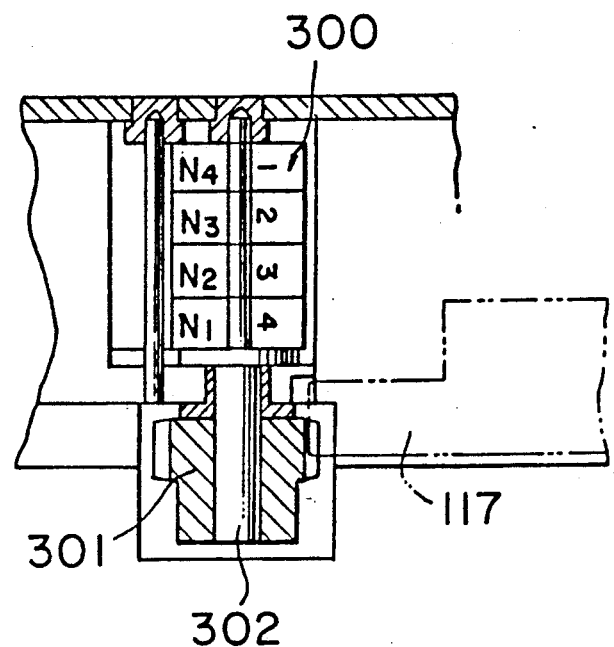
FIG. 2 is a sectional view showing the details of a counter installing portion in the rotating head mechanism in FIG. 1.

The lower gear cover 118B is formed with a window 119, and a counter 300 to be described later is installed with its display portion exposed through the window 119. FIG. 2 is a sectional view showing the details of the installed part of such a counter 300. As shown in FIG. 2, a gear 301 is mounted on the drive shaft 302 of the counter 300, and it is held in mesh with the foregoing gear 117 mounted on the lower end of the shaft 104. Although not shown in FIG. 1, such a counter is also disposed in the upper gear cover 118A, so that size adjustments can be easily done by either the drive shaft 115B or the drive shaft 115A.

Figure 3:
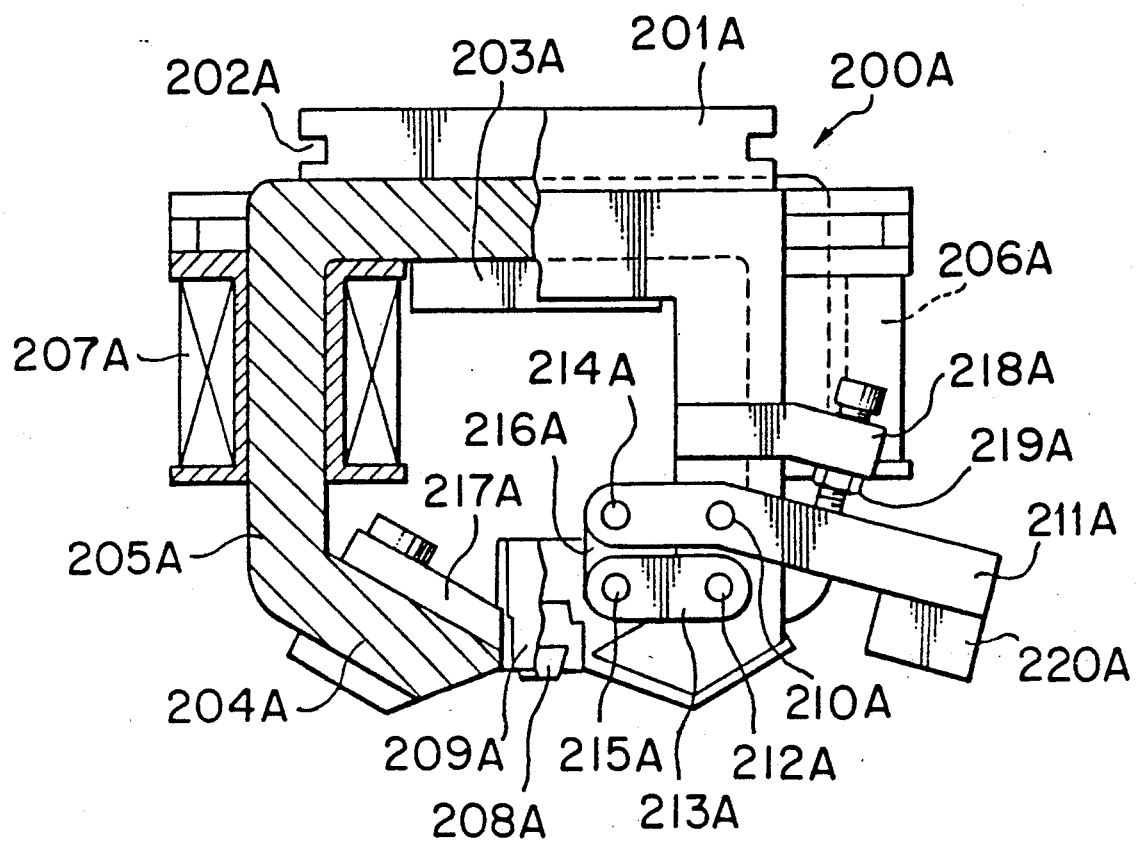
FIG. 3 is a front view of an exciting magnetic poles/detecting probes-assembly of another type which is alternative to each of exciting magnetic poles/detecting probes-assemblies in the rotating head mechanism in FIG. 1.
Figure 4:
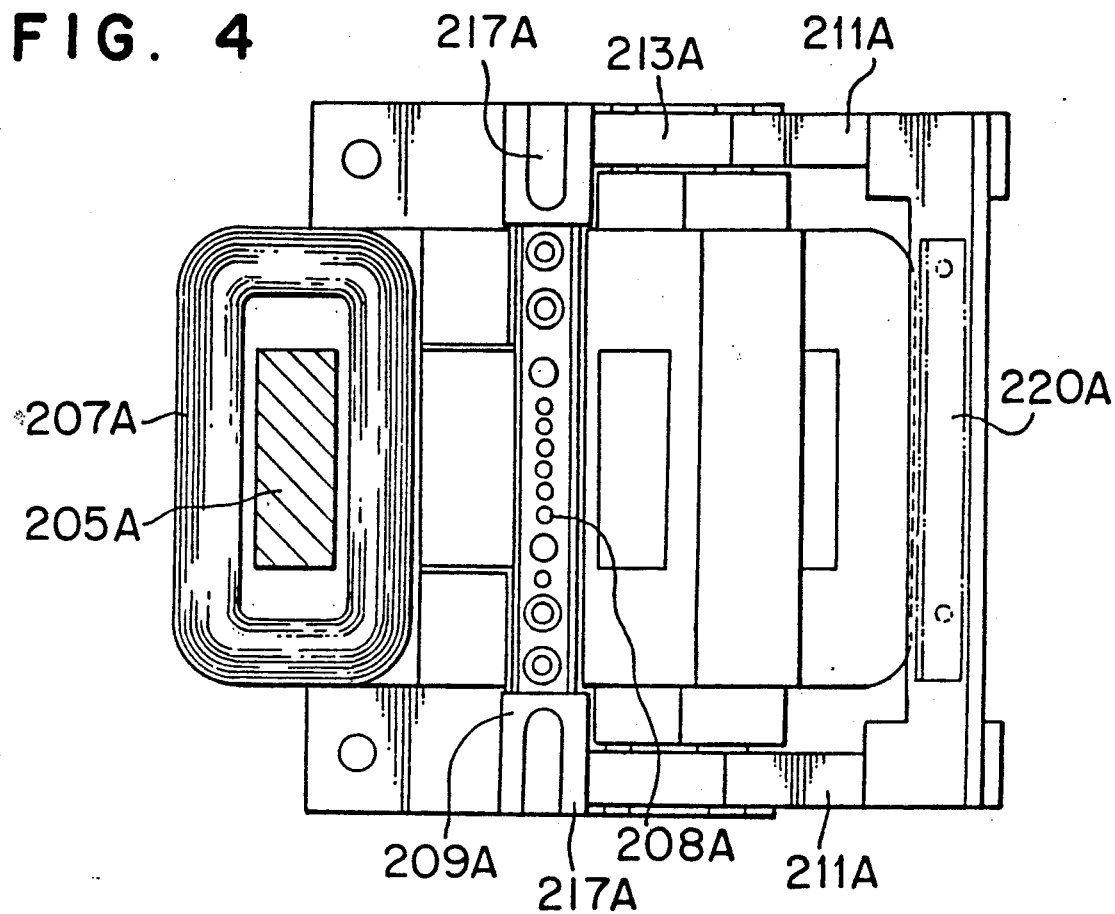
FIG. 4 is a bottom view of the exciting magnetic poles/detecting probes-assembly in FIG. 3.
Figure 5:
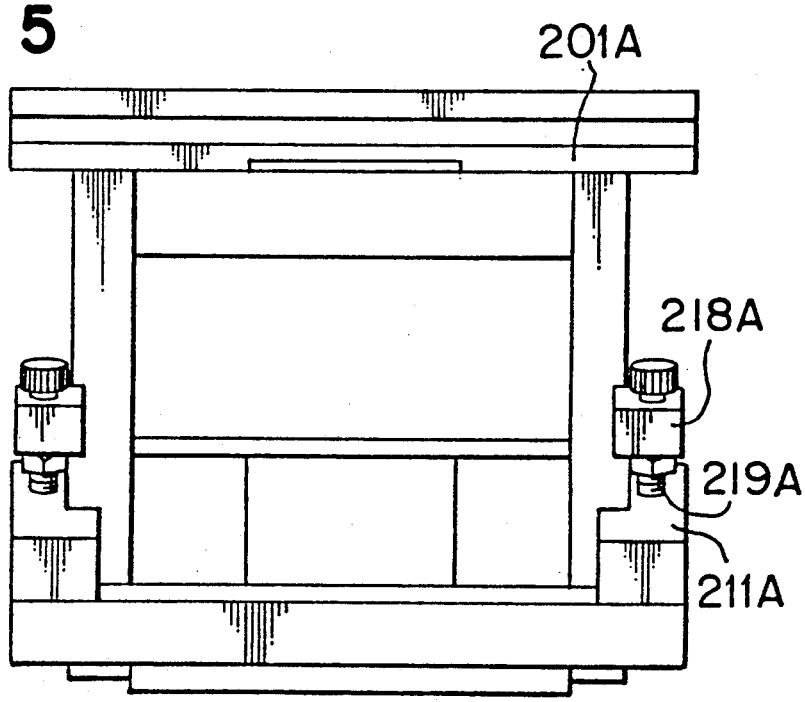
FIG. 5 is a side view of the exciting magnetic poles/detecting probe assembly in FIG. 3.

Next, the constructions of the exciting magnetic poles/detecting probes-assemblies 200A and 200B detachably mounted on the respective magnet yoke cradles 107A and 107B will be described in detail. Since the construction of the exciting magnetic poles/detecting probes-assembly 200B is the same as that of the exciting magnetic poles/detecting probes-assembly 200A, only the latter will be explained in detail, and the former shall not be especially detailed. Incidentally, the exciting magnetic poles/detecting probes-assemblies 200A, 200B shown in FIG. 1 are such that detecting probe holders are attached to movable arms 211A, 211B having no auxiliary links, and they are used for test pieces the upper limit of the applicable diameters of which is 120 mm. FIG. 3 is a front view of an exciting magnetic poles/detecting probes-assembly 200A of another embodiment which can be used instead of the exciting magnetic poles/detecting probes-assembly 200A or 200B shown in FIG. 1. The exciting magnetic poles/detecting probes-assembly 200A in FIG. 3 is such that a detecting probe holder is attached to a movable arm having an auxiliary link, and it is used for test pieces of small diameters, the upper limit of the applicable diameters of which is 80 mm. Excepting whether or not the movable arm has the auxiliary link, the exciting magnetic poles/detecting probes-assembly in FIG. 1 is substantially the same as that in FIG. 3, and hence, only the latter will be explained in detail. FIG. 4 is a bottom view corresponding to FIG. 3, and FIG. 5 is a side view corresponding to FIG. 3. As shown in these figures, the exciting magnetic poles/detecting probes-assembly 200A comprises a substantially C-shaped magnet yoke 205A which has a pair of exciting magnetic pole portions 204A opposing to each other, and exciting coils 206A and 207A which are wound round the magnet yoke 205A. The magnet yokes 204A and 205A are made of laminated silicon steel sheet. A mounting plate 201A is fixed to the magnet yoke 205A by a fixing plate 203A. Both the sides of the mounting plate 201A are formed with guide grooves 202A with which the guides 108A of the magnet yoke cradle 107A shown in FIG. 1 are brought into engagement. Besides, the movable arm 211A is attached to the right leg of the magnet yoke 205A so as to be turnable round a pivotal pin 210A. Also, the auxiliary link 213A which is turnable round a pivotal pin 212A is attached to the right leg of the magnet yoke 205A. Further, a detecting probe-mounting link 216A is attached to the left link portion of the movable arm 211A and the left end of the auxiliary link 213A by pivotal pins 214A and 215A. These links constitute a so-called parallel link motion. Attached to the auxiliary link 216A is the detecting probe holder 209A on which a plurality of detecting probes 208A are arrayed and held. As shown in FIG. 3, the magnet yoke 205A is provided with guide shoes 217A. As best shown in FIG. 4, these guide shoes 217A engage guide grooves formed in both the ends of the detecting probe holder 209A, thereby functioning to guide the vertical movements of the detecting probe holder 209A. Further, a balance weight 220A is attached to the right end of the movable arm 211A. In addition, above the movable arm 211A, a support arm 218A having an adjustable stopper 219A is attached to the magnet yoke 205A. Similarly to the foregoing, the exciting magnetic poles/detecting probes-assembly 200B comprises a magnet yoke 205B, a mounting plate 201B, the movable arm 211B, detecting probes 208B, etc.

Now, structures for mounting the exciting magnetic poles/detecting probes-assemblies 200A and 200B on the respective magnet yoke cradles 107A and 107B will be described with reference to FIG. 1. First, regarding the mounting structure of the exciting magnetic poles/detecting probes-assembly 200B, this assembly 200B is inserted in a direction perpendicular to the sheet of drawing as viewed in FIG. 1, in such a manner that the guide grooves 202B of the mounting plate 201B of this assembly 200B are brought into fit engagement with the respectively corresponding guides 108B of the magnet yoke cradle 107B. The insertion is stopped by a stopper (not shown) which is provided at the deep position of the magnet yoke cradle 107B. At the stopped position, a clamping wrench is inserted through a wrench insertion hole 120 which is provided so as to penetrate the gear cover 118B as well as the mounting frame 102B. Further, the wrench is passed through a corresponding wrench insertion hole 110 which is formed in a bolting stopper case 109B mounted on the magnet yoke cradle 107B, and a bolt 113 is pressed and turned against a compression spring 112 by the wrench. Then, the bolt 113 comes into engagement with a tapped hole provided in the mounting plate 201B, whereby the exciting magnetic poles/detecting probes-assembly 200B is fixed to the magnet yoke cradle 107B. In case of replacing the exciting magnetic poles/detecting probes-assembly 200B, operations reverse to the above may be per-formed. Since the structure and operations for mounting the exciting magnetic poles/detecting probes-assembly 200A on the magnet yoke cradle 107A are similar to the above, they shall not be repeatedly detailed.

After the exciting magnetic poles-detecting probes-assemblies 200A and 200B have been independently mounted on the respective magnet yoke cradles 107A and 107B in this way, they can be respectively moved to positions most suitable for flaw detection with respect to the outer diameter of the test piece. By way of example, when the drive shaft 115A is rotated clockwise, the shafts 103 and 104 are rotated clockwise through the intermediate gears 116 as well as the gears 117. Then, the right-handed nuts 105A and 106A are moved upwards as viewed in FIG. 1, so that the magnet yoke cradle 107A is moved upwards. Simultaneously, the left-handed nuts 105B and 106B are moved downwards as viewed in FIG. 1, so that the magnet yoke cradle 107B is moved downwards. In this manner, owing to the fact that each of the shafts 103 and 104 is formed with the right-handed external thread at its upper half and the left-handed external thread at its lower half, the exciting magnetic poles/detecting probes-assemblies 200A and 200B mounted on the respective magnet yoke cradles 107A and 107B are synchronously moved in the directions opposite to each other by the rotation of the drive shaft 115A, and they are interlockedly moved symmetrically with respect to the center of the test piece passed through the central opening of the rotating disc 101, whereby size adjustments can be made. In FIG. 1, the exciting magnetic poles/detecting probes-assembly 200A is illustrated in the state in which it is size-adjusted to the test piece 1 of large outer diameter, while the exciting magnetic poles/detecting probes-assembly 200B is illustrated in the state in which it is size-adjusted to the test piece 1' of small outer diameter. Such size adjustments can alternatively be similarly effected by rotating the drive shaft 115B.

In this embodiment, as best shown in FIG. 2, the digital counter 300 which is driven and rotated in engagement with the gear 117 is provided to count the magnitude of rotation of the drive shaft 115A or 115B, whereby a set size can be displayed at the window 119. By way of example, it is assumed that the number of teeth of the gear 114A is 40, that the number of teeth of the gear 117 is 80, and that the number of teeth of the gear 301 is 20. It is also assumed that the rotational ratio between the "4" digit $N_4$ of the decimal digital counter 300 and the gear 302 is 1:10, that the rotational ratio between the "3" digit $N_3$ and the "2" digit $N_2$ is 10:1 and that the rotational ratio between the "2" digit $N_2$ and the "1" digit $N_1$ is 10:1. Besides, the thread pitches of the nuts 105A thru 106B are assumed to be 2 mm. Then, the movement distance L of each of the nuts in the case of rotating the drive shaft 115A or 115B for the size adjustments one revolution becomes:

$$L = 40/80 \times 2 = 1 (mm/revolution)$$

The scale N of the counter 300 on this occasion becomes as follows:

$$N_1 = 40/20 \times 10 = 20$$

Here, the digit $N_1$ is such that numerals 0-9 are distributed in ten equal parts. On the basis of $N_2/N_1 = 1/10$, therefore, $N_1 = 20$ is distributed into $N_1 = 0$ and $N_2 = 2$. In consequence, the counter 300 displays "0020" for the distance $L = 1$ mm/revolution. When this display is read as 2.0, the adjustment size can be indicated with accuracy by the order of 0.1 mm.

When the rotating disc 101 is rotated after the size adjustment as stated before, the individual detecting probes 208A and 208B precisely detect any flaw in opposed contact with the outer surface of the test piece under a predetermined pressure which depends upon the number of revolutions and the weight value of the balance weight 220A mounted on each of the movable arms 211A and 211B. In this case, the opposing areas and opposing spacings between the exciting magnetic pole portions 204A and the test piece and the relative mechanical positions between the detecting probes and the test piece have important relations to the capability of the flaw detection. The detecting probes 208A and 208B depress the test piece by means of the centrifugal force of the balance weight 220A which is mounted on the movable arm 211A and which moves round the pivotal pin 210A fixed to the exciting magnet yoke 205A. When the test piece enters, the fore end thereof pushes up the detecting probes 208A and 208B against depressive forces based on the centrifugal force. When the magnitudes of the push-up are excessive, the detecting probes 208A and 208B might damage. That is, the movable arm stopper 219A functions to set the movable extent of the movable arm 211A, namely, the lower limit of the forces of the detecting probes 208A and 208B in the depressing directions thereof in order to fulfill such conditions as the appropriate positional relations between the detecting probes and the exciting magnetic pole portions 204A, the prevention of the mechanical damage at the arrival of the fore end of the test piece, and the shortening of a responsive conformation time according to which the detecting probes come into touch with the outer surface of the test piece immediately after the arrival of the fore end of the test piece.

In FIG. 1, reference numerals 121 and 122 designate a connecting plug seat for supplying exciting power to the exciting magnetic poles/detecting probes-assembly 200A, and a connecting plug seat for deriving signals from the detecting probes of this assembly, respectively. Besides, reference numerals 123 and 124 designate a connecting plug seat for supplying exciting power to the exciting magnetic poles/detecting probes-assembly 200B, and a connecting plug seat for deriving signals from the detecting probes of this assembly, respectively.

Figure 6:
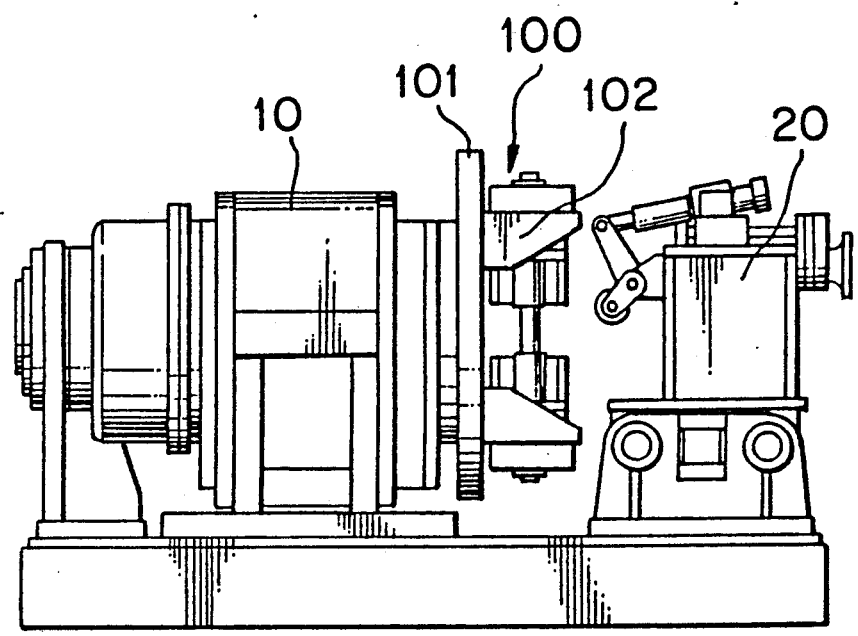
FIG. 6 is a side view exemplifying the rotary type leakage-flux flaw detector which uses the rotating head in FIG. 1.

FIG. 6 shows a side view of a rotary type MFL flaw detector 10 which is equipped with the rotating head mechanism 100 as stated above. Reference numeral 20 indicates an exit-side guide mechanism which is disposed on the exit side of the flaw detector 10 and which serves to guide the transportation of the test piece while applying a centripetal force to this test piece.

Since the rotating head mechanism of a rotary type leakage-flux flaw detector according to the present invention is constructed as described before, it can demonstrate the following effects:

(1) A pair of exciting magnetic poles/detecting probes-assemblies opposing to each other can be simultaneously moved only by a single manual operation to the optimum positions for the outer diameter of a bar or tube to be inspected, so that the efficiency of jobs involved in daily multikind and small-quantity production can be improved. On this occasion, it is also possible to directly read a size value during a size adjustment by means of a digital counter.

(2) The exciting magnetic poles/detecting probes-assemblies are independently attachable to and detachable from the yoke cradles of a rotating head mechanism, whereby the replacement and maintenance of the exciting magnetic poles/detecting probes-assemblies can be facilitated. Moreover, on this occasion, the attachment or detachment of the exciting magnetic poles/detecting probes-assembly can be readily done in such a way that a wrench is inserted through a penetrating wrench insertion hole from a size adjustment portion side, and that a flanged bolt is clamped or loosened. In this case, the flanged bolt is normally urged upwards from the fitting plane thereof by a compression spring, whereby the flanged bolt can be prevented from coming below the fitting plane due to its own weight and then forming an obstacle to the magnet yoke attachment or detachment.

(3) The detecting probes of the exciting magnetic poles/detecting probes-assembly are held on a movable arm, whereby they are capable of automatic withdrawal at the time of stop and are also capable of centripetal movements through a link motion, so that they can be automatically withdrawn when a bending test piece enters. Since a balance weight to be mounted on the movable arm can be chosen at will, the depressive forces of the detecting probes are selected with ease.

What is claimed is:

1. A rotating head mechanism of a rotary type AC magnetic flux leakage flaw detector, comprising a rotating disc which has an opening for passing a test piece for flaw detection, mounting frames which are secured to said rotating disc so as to oppose each other with said opening located therebetween, shafts which are provided to extend between said mounting frames and the ends of which are pivotally supported by said mounting frames each of which has external threads of senses opposite to each other at a position on one side of said opening and a position on the other side thereof, a first nut which engages the external thread of one sense in said external threads of each shaft, a second nut which engages the external thread of the other sense in said external threads of each shaft, a first cradle which is coupled to the first nuts, a second cradle which is coupled to the second nuts, a first exciting magnetic poles/detecting probes-assembly which is mounted on said first cradle, a second exciting magnetic poles/detecting probes-assembly which is mounted on said second cradle, and rotation drive means for rotating said shafts, wherein when said shafts are rotated by said rotation drive means, said first and second nuts are moved in a direction in which they come near to each other or away from each other along said shafts, thereby making it possible to change an opposing spacing in a diametrical direction of said opening, between said first and second exciting magnetic poles/detecting probes-assemblies respectively mounted on said first and second cradles.

2. A rotating head mechanism as claimed in claim 1, wherein said rotation drive means has digital counter means associated therewith, said digital counter means serving to digitally display a magnitude of rotation of said each shaft as based on said rotation drive means so as to indicate the opposing spacing.

3. A rotating head mechanism as claimed in claim 2, wherein said exciting magnetic poles/detecting probes-assemblies are mounted on said respective cradles in a manner to be capable of sliding insertion and to be detachable.

4. A rotating head mechanism as claimed in claim 3, wherein detecting probes in both of said exciting magnetic poles/detecting probes-assemblies are mounted on automatic swinging means, and said automatic swinging means confronts said detecting probes between exciting magnetic poles of both assemblies and holds them in predetermined relations to corresponding surface parts of the test piece passing through said opening of said rotating disc.

* * * * *